(12) United States Patent
Wanders et al.

(10) Patent No.: US 9,103,964 B2
(45) Date of Patent: Aug. 11, 2015

(54) INTRAOCULAR LENSES ESSENTIALLY FREE FROM GLISTENINGS

(75) Inventors: Bernardus Franciscus Maria Wanders, Angerlo (NL); Henk Haitjema, Eerbeek (NL)

(73) Assignee: Oculentis Holding B.V., Eerbeek (NL)

( * ) Notice: Subject to any disclaimer, the term of this patent is extended or adjusted under 35 U.S.C. 154(b) by 413 days.

(21) Appl. No.: 12/279,290

(22) PCT Filed: Feb. 14, 2007

(86) PCT No.: PCT/NL2007/050059
§ 371 (c)(1),
(2), (4) Date: Aug. 13, 2008

(87) PCT Pub. No.: WO2007/094665
PCT Pub. Date: Aug. 23, 2007

(65) Prior Publication Data
US 2009/0054978 A1 Feb. 26, 2009

Related U.S. Application Data

(60) Provisional application No. 60/772,895, filed on Feb. 14, 2006.

(30) Foreign Application Priority Data
Feb. 14, 2006 (EP) ................................ 06101664

(51) Int. Cl.
| | | |
|---|---|---|
| A61F 2/16 | (2006.01) |
| B32B 17/10 | (2006.01) |
| B41J 2/16 | (2006.01) |
| A61K 6/083 | (2006.01) |
| A61L 24/00 | (2006.01) |
| G02B 1/04 | (2006.01) |
| A61L 27/16 | (2006.01) |
| A61L 27/50 | (2006.01) |

(52) U.S. Cl.
CPC ............. *G02B 1/043* (2013.01); *A61L 27/16* (2013.01); *A61L 27/50* (2013.01); *A61L 2430/16* (2013.01)

(58) Field of Classification Search
USPC ............................................. 623/6.56, 6.58
See application file for complete search history.

(56) References Cited

U.S. PATENT DOCUMENTS

| | | | |
|---|---|---|---|
| 5,132,430 A | 7/1992 | Gaudiana et al. | |
| 5,290,892 A | 3/1994 | Namdaran et al. | |
| 5,331,073 A | 7/1994 | Weinschenk et al. | |
| 5,693,095 A | 12/1997 | Freeman et al. | |
| 5,861,031 A | 1/1999 | Namdaran et al. | |
| 5,945,498 A | 8/1999 | Hopken et al. | |
| 6,015,842 A * | 1/2000 | LeBoeuf et al. | 522/64 |
| 6,140,438 A | 10/2000 | Ojio et al. | |
| 6,326,448 B1 | 12/2001 | Ojio et al. | |
| 6,329,485 B1 | 12/2001 | Vanderbilt | |
| 6,653,422 B2 * | 11/2003 | Freeman et al. | 526/259 |
| 6,657,032 B2 | 12/2003 | Vanderbilt | |
| 6,833,391 B1 | 12/2004 | Chisholm et al. | |
| 7,297,160 B2 * | 11/2007 | Salamone et al. | 623/6.56 |
| 2003/0130460 A1 | 7/2003 | Freeman et al. | |
| 2003/0224250 A1 | 12/2003 | Setthachayanon et al. | |
| 2005/0049376 A1 | 3/2005 | Chisholm et al. | |
| 2005/0055090 A1 | 3/2005 | Lai et al. | |
| 2007/0010883 A1 * | 1/2007 | Mentak | 623/6.58 |
| 2009/0247661 A1 * | 10/2009 | Muller-Lierheim et al. | 522/180 |

FOREIGN PATENT DOCUMENTS

| | | |
|---|---|---|
| CN | 1-44666 A | 8/1990 |
| EP | 0 485 197 B1 | 10/1996 |
| WO | WO 99/53347 A | 10/1999 |
| WO | WO-2007/062864 | 6/2007 |

OTHER PUBLICATIONS

English abstract of CN 1044666 (A), Shuojian Jiang, et al, published Aug. 15, 1990, data supplied from the *espacenet* database—Worldwide.

Handbook of Chemistry & Physics, 59th Ed., CRC Press, Boca Raton, Florida, 1978-1979.

* cited by examiner

*Primary Examiner* — Thomas J Sweet
*Assistant Examiner* — Tiffany Shipmon
(74) *Attorney, Agent, or Firm* — Gilberto M. Villacorta; Sunit Talapatra; Foley & Lardner LLP

(57) ABSTRACT

The present invention relates a method for manufacturing an intraocular lens in a closed mold, wherein an acrylic monomer composition containing a single high refractive index monomer according to formula (I): is polymerized by employing an initiator that is activated by light having a wavelength of 390 nm or more.

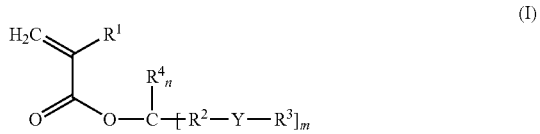

(I)

23 Claims, No Drawings

INTRAOCULAR LENSES ESSENTIALLY FREE FROM GLISTENINGS

SUBJECT OF THE INVENTION

The present invention relates to intraocular lenses manufactured from copolymers comprising a single high refractive index monomer, wherein the intraocular lenses are essentially free from glistenings.

BACKGROUND OF THE INVENTION

With the recent advances in small-incision cataract surgery, increased emphasis has been placed on developing soft, foldable materials suitable for use in artificial intraocular lenses ("IOL"). Materials that are commonly used for such lenses include hydrogels, silicones and acrylic polymers.

Hydrogels have a relatively low refractive index which makes them less desirable materials because of the thicker lens optic that is necessary to achieve a given refractive power. Silicones have a higher refractive index than hydrogels, but tend to unfold explosively after being placed in the eye in a folded position. Explosive unfolding can potentially damage the corneal endothelium and/or rupture the natural lens capsule. Acrylic polymers are currently the material of choice since they typically have a high refractive index and unfold more slowly or controllably than silicone materials. U.S. Pat. No. 5,290,892 and U.S. Pat. No. 5,331,073, for example, disclose high refractive index, acrylic copolymers suitable for use as an IOL material.

An important feature in the design of modern IOL's made of high refractive index material is that lenses can be made thinner which allows for a specific design of the lens being rolled in smaller dimensions. This consequently necessitates a smaller incision size in lens cataract surgery with the advantage of reduced risks for complications like astigmatism or complications related to incision healing.

A further requirement for IOL material is that rolling the lens does not induce tears or wrinkles so that after release of the lens from the cartridge nozzle the lens unfolds in a controlled way to its pre-rolled dimensions without its optical quality being compromised. The material must also be stiff enough such that thin high refractive index lenses do not deform when residing in the eye. After all, lenses must remain flat to retain their optical properties.

A known method for manufacturing IOL's comprises polymerization of the acrylic monomer composition in open moulds where after the raw IOL is further mechanically processed by lathing, drilling, grinding and the like. However, it is highly advantageous to polymerise the acrylic monomer composition in a closed castmould whereby a ready-to-use IOL is directly formed. Such methods wherein in particular closed castmoulds are employed, on the other hand, might give rise to the formation of vacuoles filled with air or gas in the polymerised material. Such vacuoles are in particular formed when thermal free radical initiators such as azo initiators are used that form gases as byproducts. Upon implantation of the IOL, these vacuoles are hydrated thereby giving rise to the formation of white dots due to reflection of light, a phenomenon known in the art as "glistenings". In fact, these vacuoles containing moisture have a refractive index that is different from that of the IOL material.

A solution for this problem that is provided by the prior art is employing an acrylate monomer composition comprising at least one hydrophobic, high refractive index IOL-forming monomer in conjunction with a small amount of a hydrophilic monomer. By the incorporation of the latter, the hydrophilicity of the IOL is improved so that any moisture is better dispersed within the IOL.

For example, U.S. Pat. No. 5,693,095 discloses acrylic monomer compositions comprising a hydrophilic monomer, e.g. 2-hydroxyethyl acrylate, and a high refractive index, IOL-forming, hydrophobic aryl acrylic monomer having the general formula:

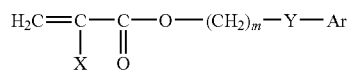

wherein X is hydrogen or methyl, m is an integer of 0-6, Y is a direct bond, O, S or NR (R may be alkyl) and Ar is an optionally substituted aromatic group. The acrylic monomer compositions further comprise a crosslinker such as 1,4-butanediol diacrylate. The polymerization of the acrylic monomer composition is preferably thermally initiated by using peroxy free radical initiators. The polymerized materials are said to be substantially free of glistenings.

Similarly, U.S. Pat. No. 6,140,438 and U.S. Pat. No. 6,326,448 disclose an acrylic monomer composition comprising an aromatic ring containing (meth)acrylate monomer (A) of the formula:

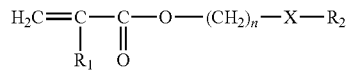

wherein $R_1$ is hydrogen or methyl, n is an integer of 0-5, X is a direct bond or oxygen, and $R_2$ is an optionally substituted aromatic group, a hydrophilic monomer (B), an alkyl(meth)acrylate monomer (C) wherein the alkyl group has 1-20 carbon atoms, and a crosslinker (D). The polymerization can be conducted by any conventional method, i.e. thermally by using azo or peroxide initiators or by irradiation with electromagnetic waves such as UV. The polymerized material has a water absorptivity of 1.5 to 4.5 wt. % and has an improved transparency. The polymerized materials are further mechanically processed into IOL's.

U.S. Pat. No. 6,329,485 and U.S. Pat. No. 6,657,032 disclose an acrylic monomer composition comprising a high refractive index aromatic acrylate monomer, a hydrophilic monomer in an amount higher than that of the high refractive index aromatic acrylate monomer, and a crosslinker. The polymerization is preferably conducted by thermal initiation in the presence of azo or peroxide initiators, preferably the azo initiator 2,2'-azobis(isobutyronitril). After polymerization, the polymerized materials are further mechanically processed as described above to form IOL's.

The prior art discussed above all employ acrylic monomer compositions comprising at least two IOL-forming monomers, i.e. a hydrophobic monomer and a hydrophilic monomer, and a crosslinker not only to improve the hydrophilicity of the polymerised material, but also to adjust the glass transition temperature to around ambient temperature or below (as otherwise the lenses cannot be folded without damaging the lens). However, this has the disadvantage that the refractive index is also lowered which is obviously undesired.

U.S. Pat. No. 6,653,422 discloses acrylic monomers having a very high refractive index which have the formula:

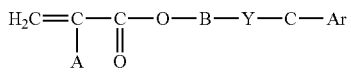

wherein it is preferred that A is hydrogen or methyl, B is —(CH$_2$)$_m$— wherein m is an integer of 2-5, Y is a direct bond or oxygen, C is —(CH$_2$)$_w$— wherein w is an integer of 0 or 1 and Ar is phenyl. The IOL material is made from these monomers only and a cross-linking monomer. The refractive index is at least 1.50, de glass transition temperature is preferably below 25° C. and the elongation is at least 150%. According to the examples, the copolymer made of 3-benzoyloxypropyl methacrylate (B=3, Y=O, w=1, Ar=phenyl) and polyethylene glycol 1000 dimethyacrylate has the highest refractive index (dry state) which is 1.543 (Example 11).

US 2005/0049376 discloses curable (meth)acrylate compositions suitable for optical articles and in particular for light management films. Apart from a high refractive index, these compositions when cured have desirably a high glass transition temperature for shape retention during storage and use of the light management films. Tables 7 and 8 disclose glass transition temperatures of 41°-62° C. The refractive index of a composition made of 1,3-bis(thiophenyl)propane-2-yl acrylate and the diacrylate of tetrabromo bisphenol A diepoxide has a refractive index as high as 1.6016 (Example 14). Although generally having a high refractive index, the compositions are obviously unsuitable for IOL applications because of their high glass transition temperatures.

U.S. Pat. No. 6,015,842 discloses a method for preparing a foldable, acrylic, high refractive index ophthalmic material from a composition comprising a hydrophilic crosslinker, e.g. polyethyleneoxide di(meth)acrylate, one or more hydrophilic monomers, a UV absorbing chromophore and a benzoyl phosphine oxide photoinitiator which can be activated by blue light having a wave length in the range of 400-500 nm.

US 2005/0055090 discloses an intraocular lens that is made from a high refractive index monomer, a photoinitiator that can be activated by blue light having a wave length of above 500 nm. The high refractive index monomer is for example 2-ethylphenoxy (meth)acrylate and 2-ethylthiophenyl (meth)acrylate.

It is therefore an object of the invention to provide a method for manufacturing IOL's having a high refractive index as well as a low glass transition temperature, in particular a glass transition temperature of lower than 25° C.

It is a further object of the invention to provide a method for manufacturing IOL's that are essentially free from glistenings.

It is another object of the invention to provide a method for manufacturing IOL's that can be conducted in closed castmoulds.

In addition, it is an object of the invention to provide a method for the manufacturing of IOL's wherein an acrylic monomer composition is used that contains a single IOL-forming monomer.

SUMMARY OF THE INVENTION

The present invention relates to a method for manufacturing an intraocular lens, wherein an acrylic monomer composition containing a single high refractive index monomer according to formula (I):

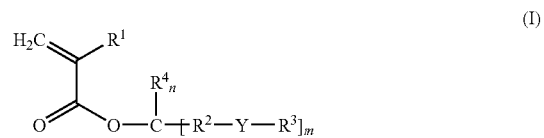

wherein R$^1$ is H or CH$_3$;
R$^2$ is a C$_1$-C$_3$ alkylene or —C$_1$-C$_3$ alkylene)-Y—(C$_1$-C$_3$ alkylene)-;
Y is O or S;
R$^3$ is C$_6$-C$_{18}$ aryl or heteroaryl;
R$^4$ is H or linear or branched C$_1$-C$_6$ alkyl;
m+n=3;
n=0, 1 or 2; and
m=1, 2 or 3;
is polymerized by employing an initiator that is activated by light having a wavelength of 390 nm or more.

The present invention also relates to an intraocular lens that is obtainable according the method of the invention.

DETAILED DESCRIPTION OF THE INVENTION

The method according to the invention can conveniently be performed in a closed castmould and provides ready-to-use IOL's, i.e. that minimal (e.g. only cutting) or no further mechanical processing is necessary. In addition, the IOL's formed by the method according to the present invention are essentially free from glistenings. A test for evaluating the presence of glistenings is disclosed in U.S. Pat. No. 5,693, 095, incorporated by reference for the US patent practice.

According to the present invention, the following definitions apply.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

An alkyl group is to be understood as a linear or branched alkyl group e.g. having 1 to 6 carbon atoms. Examples of such alkyl groups include methyl, ethyl, 1-propyl, 2-propyl, 1-butyl, 2-butyl, 1-pentyl, 1-hexyl and the like.

An alkylene group is to be understood as a linear or branched alkylene group having 1 to 3 carbon atoms, e.g. 1,3-propanediyl (—CH$_2$—CH$_2$—CH$_2$—) and ethanediyl (—CH$_2$—CH$_2$—).

An aryl group is to be understood as an aryl group having 6 to 18 carbon atoms. The aryl group may be substituted or unsubstituted. If the aryl group is substituted, it is preferred that they aryl group is substituted with 1 to 5 substituents, preferably 1 to 3 substituents, selected from the group consisting of halo, C$_1$-C$_4$ alkyl, C$_1$-C$_4$ alkyl-O—, C$_1$-C$_4$ alkyl-S—, C$_1$-C$_4$ haloalkyl, C$_1$-C$_4$ haloalkyl-O— and C$_1$-C$_4$ haloalkyl-S—. The aryl group may also be an annelated aryl group such as naphtyl and anthracenyl.

A heteroaryl group is to be understood as an aryl group having 6 to 18 carbon atoms and comprising one to three, preferably one to two heteroatoms selected from the group consisting of nitrogen, oxygen and sulphur. Suitable examples of heteroaryl groups include imidazolyl, furanyl, isoxazolyl, pyranyl, pyrazinyl, pyrazolyl, pyridyl and the like. For the nomenclature of heteroaryl groups, reference is made to Handbook of Chemistry & Physics, 59$^{th}$ Ed., CRC Press, Boca Raton, Fla., 1978-1979. The heteroaryl group may also be an annelated heteroaryl group such as indolyl and benzothiazolyl.

The high refractive index monomers according to formula (I) are hydrophobic in nature. According to a first preferred embodiment of the present invention, n is 0 and m=3. According to a second preferred embodiment of the present invention, n is 1 and m is 2.

It is furthermore preferred that Y is S.

Additionally, if $R^4$ is substituted, it is preferably substituted by $C_1$-$C_4$ alkyl, $C_1$-$C_4$ alkyl-O— or $C_1$-$C_4$ alkyl-S—. However, R4 is most preferably unsubstituted and is most preferably phenyl.

US 2005/0049376 discloses that high refractive index monomers such as those according to formula (I) may be coloured due to the formation of byproducts during the synthesis of the high refractive index monomers. However, for IOL's it is undesired to have inadvertently coloured polymeric materials. According to the present invention, the high refractive index monomers according to formula (I) are therefore preferably purified to render them essentially colourless prior to the polymerization reaction. A suitable technique to purify the high refractive index monomers according to formula (I) are know to the person skilled in the art and include for example chromatography and treatment with active carbon.

According to the present invention, it is preferred that the initiator is selected from the group of thermal free radical initiators like peroxides or azo-initiators like 2,2'-Azobis(2,4-dimethylvaleronitrile). However, it is more preferred that the initiator is selected from the group consisting of phosphine oxide photoinitiators, ketone-based photoinitiators and benzoin photoinitiators since those initiators do not give rise to the formation of gaseous byproducts. Most preferably, the initiator is a phosphine oxide photoinitiator. Suitable examples of such phosphine oxide photoinitiators include the IRGACURE® and DAROCURE™ series of phosphine oxide initiators available from Ciba Specialty Chemicals, the LUCIRIN® series available from BASF and the ESACURE® series. The photoinitiators employed in the method according to the present invention can be activated by irradiation with light having a wavelength of 340 nm or more, preferably 390 nm or more. Even more preferred is that the light has a wave length of 390 nm to 500 nm (UV/VIS-irradiation; this particular region is also known in the art as "blue-light irradiation"). Ketone-based photoinitiators and benzoin photoinitiators are preferably used in combination with light having a wave length of 340 nm or more, preferably a wave length of 340-500 nm.

Additionally, it is preferred that the acrylic monomer composition comprises a crosslinker, preferably selected from the group consisting of terminally ethylenically unsaturated compounds having more than one unsaturated group, preferably a (meth)acrylate group. Suitable cross-linking monomers according to this fourth preferred embodiment of the present invention include:
ethylene glycol dimethacrylate;
diethylene glycol dimethacrylate;
allyl methacrylate;
2,3-propanediol dimethacrylate; and
1,4-butanediol dimethacrylate.

The use of a crosslinker is in particular preferred in that water and moisture are better retained thereby reducing glistening. To that end, a hydrophilic monomer such as hydroxylethyl acrylate may be used as well in combination with the single high refractive index monomer.

According to a first preferred embodiment of the present invention, the crosslinker is a multifunctional (meth)acrylate monomer which comprises at least two (meth)acrylate moieties. According to this embodiment, the crosslinker is represented by the general formula (II):

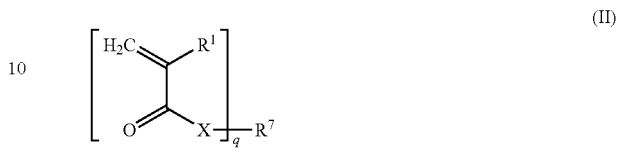

wherein:
$R^1$ is H or $CH_3$;
$R^7$ is substituted or unsubstituted $C_1$-$C_{300}$ alkyl, aryl, alkaryl, arylalkyl or heteroaryl;
X=O; and
q=2, 3 or 4.

If substituted, the substituents of $R^7$ are preferably selected from the group consisting of halo, $C_1$-$C_4$ alkyl, $C_1$-$C_4$ haloalkyl, $C_1$-$C_4$ alkyl-O—. $C_1$-$C_4$ alkyl-S—, $C_1$-$C_4$ haloalkyl-O—, $C_1$-$C_4$ haloalkyl-S— and OH—.

Suitable examples of crosslinkers according to this preferred embodiment are e.g. disclosed in U.S. Pat. No. 6,653,422 which is incorporated by reference for the US patent practice.

According to a second preferred embodiment of the present invention, the cross-linking monomer is a dendritic, star or hyperbranched (co)polymer having terminal OH end groups that are partly or completely esterified with (meth)acrylic acid. For example, three arm to six arm polyethoxylates are known in the art wherein trimethylolpropane, pentaerythritol or trimethylol propane ethoxylate are used as the core. Another example is the Boltorn polymer series, in particular H20, H30 and H40 that are manufactured by Perstorp AB.

According to a third preferred embodiment of the invention, the crosslinker is a hydrophilic crosslinker. This third preferred embodiment is preferred over the first and second preferred embodiments.

The hydrophilic crosslinker according to the third preferred embodiment has the formula (III):

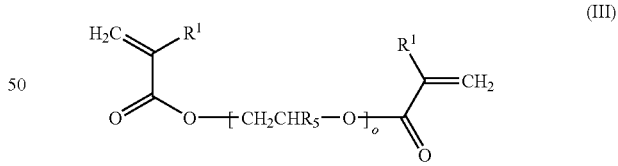

wherein $R^1$ and $R^5$ are independently H or $CH_3$; and
o is such that the number-average molecular weight is about 200 to about 2000.

However, according to the invention it is most preferred that o is 1-5.

Preferably, $R^1$ is $CH_3$. It is also preferred that $R^5$ is H.

Generally, only one crosslinker will be present in the acrylate monomer compositions. However, combinations of crosslinkers may be desirable.

The acrylic monomer composition may comprise the high refractive index monomer according to formula (I) and the crosslinker in various amounts which is inter alia dependent from the desired product properties, e.g. glass transition temperature, mechanical properties such as elongation. However, to provide high refractive index material, it is necessary that the acrylate monomer composition comprises at least 50 wt. % of high refractive index monomer according to formula (I), preferably at least 60 wt. %, more preferably at least 70 wt. %, even more preferably at least 80 wt. % and in particular at least 90 wt. %, based on the total weight of the acrylate monomer composition. The upper limit for the high refractive index monomer according to formula (I) is 99.8 wt. %.

The acrylic monomer composition will further comprise the crosslinker in an amount of 0.1 to 20.0 wt. %, preferably 0.5 to 15.0 wt. %, based on the total weight of the acrylate monomer composition.

According to the invention, it is preferred to employ 0.1 to 3.0 wt. %, more preferably 0.5 to 2.5 wt. % of the initiator, based on the total weight of the acrylate monomer composition.

According to the present invention, the acrylate monomer composition can be polymerised directly in a mould, preferably a closed castmould. However, in certain circumstances it may be advantageous to prepolymerise the acrylate monomer composition and to finalise curing of the prepolymerised acrylate monomer composition in the mould, preferably a closed castmould.

In addition to the monomers and crosslinkers disclosed above, the polymer composition according to the present invention may contain a total of up to about 10% by weight of additional components, based on the total weight of the monomer mixture, which serve other purposes, such as UV absorbers. Suitable UV absorbers include benzotriazole compounds such as the Tinuvin series. An example is 2-(2'-hydroxy-3'-methallyl-5'-methylphenyl)benzotriazole (Tinuvin P). If present, UV absorber is present in an amount of 0.1 to 5.0 wt. %, preferably 0.2 to 4.0 wt. %, based on the total weight of the acrylate monomer composition.

The present invention also relates to an intraocular lens, preferably a flexible intraocular lens, obtainable by the method according to the invention. The intraocular lens has a glass transition temperature $T_g$ of less than 25° C., preferably less than 15° C., more preferably less than 10° C., which can be attained by using the hydrophobic high refractive index monomer according to formula (I). Additionally, the IOL has a refractive index of at least 1.50, preferably at least 1.55 and more preferably at least 1.60. Furthermore, the intraocular lens has excellent mechanical properties, e.g. an elongation of at least 150%, preferably at least 200% and more preferably at least 300%. A suitable method for measuring elongation is for example disclosed in U.S. Pat. No. 6,653,422, incorporated by reference herein for the US patent practice.

Example

The HRI Monomers were synthesized as described below. Their purity was typically 95+%. Other ingredients were purchased off the shelf from outside vendors. Typically 99+% quality materials were used. Synthesis was performed in suitable laboratory glassware. Blue light irradiations for curing were performed using a suitable blue light source under a suitable atmosphere at RT (Room Temperature).

Synthesis of the HRI Monomer 1,3-bis(phenylthio)propan-2-yl Methacrylate

Synthesis of the precursor 1,3-bis(phenylthio)propan-2-ol.

Thiophenol (54.1 mL, 529.1 mmol, 2.0 eq) was added to a threeneck flask and cooled in an ice/water bath, under a nitrogen atmosphere. KOH (29.68 g, 529.1 mmol, 2.0 eq) was dissolved in isopropanol (600 mL) and added to the thiophenol. Epichlorohydrin I (20.7 mL, 264.5 mmol, 1.0 eq) was added drop wise in 20 min. An exothermic reaction was observed, and the temperature was kept below 28° C. A white precipitate formed during addition. The mixture was heated at 65° C. for 1 h. The mixture was poured in aq. 20% citric acid sol. (500 mL). t-Butylmethyl ether (500 mL) was added and the layers were separated. The water layer was extracted with t-butylmethyl ether (250 mL). The combined organic layers were washed subsequently with brine (250 mL), sat. aq. NaHCO$_3$ sol. (500 mL) and brine (500 mL), dried over Na$_2$SO$_4$ and concentrated in vacuo yielding a yellow oil.

The monomer 1,3-bis(phenylthio)propan-2-yl methacrylate.

Alcohol 1,3-bis(phenylthio)propan-2-ol (20.0 g, 72.46 mmol, 1.0 eq) was dissolved in THF (400 mL), under nitrogen atmosphere. Et3N (17.3 mL, 123.2 mmol, 1.7 eq) and a few crystals of 4-methoxyphenol were added. Methacrylolylchloride (10.6 mL, 108.7 mmol, 1.5 eq) (freshly distilled) was added. The solution was warmed to 50° C. and stirred for 48 h. The mixture was concentrated in vacuo and dichloromethane (300 mL) was added. The mixture was poured in cold sat. aq. NH$_4$Cl sol. (500 mL). The organic layer was separated from the water layer. The water layer was extracted with dichloromethane (2×250 mL). The combined organic layers were washed with water (2×500 mL), dried over Na$_2$SO$_4$ and concentrated in vacuo yielding 25.9 g (>100%) of a brown oil, which was purified by filtration over Silica (100% heptane to 5% ethyle acetate in heptane). Yield was 24.4 g (97%) of an essentially colourless low viscosity oil. The monomer was stabilised with 100 ppm mono-methyl-ether hydroquinone. The identity of the monomer was confirmed by NMR, GC-MS and HPLC-MS.

Formulation Using a HRI Monomer.

The HRI monomer 1,3-bis(phenylthio)propan-2-yl methacrylate (M2) was formulated in the following composition under subdued light conditions to avoid premature decomposition of the photoinitiator:

| Material | Wt % |
| --- | --- |
| M2 | 92.85 |
| EGDMA* | 6.0 |
| UV-blocker** | 1.0 |
| Irg 819*** | 0.15 |

*Ethylene Glycol Di Methacrylate
**A methacrylate modified benzotriazole based material from Sigma-Aldrich
***A phosphineoxide based photoinitiator from Ciba Specialty Chemicals After complete dissolution of all materials the formulation was ready for use.

Castmoulding

The photocurable HRI monomer containing composition as prepared previously was added to a polymeric castmould consisting of a lower and a upper half enclosing a space in the form of an IOL moulding. The mould was irradiated with blue light under suitable conditions for the appropriate amount of time. After opening of the mould the IOL moulding was removed and inspected for quality. It was found that the moulding consisted of an optically transparent material with the desired properties for a suitable IOL material. The moulding did not tear on folding, and returned to the original dimensions when the folding force was released. Folding marks were not visible after folding, while elongation was about 100%.

The invention claimed is:

1. A method for manufacturing an flexible intraocular lens, the method comprising polymerizing in a closed mould an acrylic monomer composition comprising a single high refractive index monomer according to formula (I):

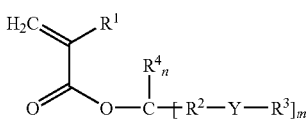

wherein $R^1$ is H or $CH_3$;
$R^2$ is a $C_1$-$C_3$ alkylene or —($C_1$-$C_3$ alkylene)-Y—($C_1$-$C_3$ alkylene)-;
Y is O or S;
$R^3$ is $C_6$-$C_{18}$ aryl or heteroaryl;
$R^4$ is H or linear or branched $C_1$-$C_6$ alkyl;
m+n=3;
n=0 or 1; and
m=2 or 3;
in the presence of an initiator that is activated by light having a wave length of 390 nm or more, wherein the intraocular lens is a flexible lens.

2. The method according to claim 1, wherein n is 0 and m=3.

3. The method according to claim 1, wherein n is 1 and m is 2.

4. The method according to claim 1, wherein Y is S.

5. The method according to claim 1, wherein $R^3$ is phenyl.

6. The method according to claim 1, wherein the initiator is selected from the group consisting of phosphine oxide photoinitiators, ketone-based photoinitiators and benzoin photoinitiators.

7. The method according to claim 1, wherein the acrylic monomer composition further comprises a hydrophilic crosslinker.

8. The method according to claim 7, wherein the hydrophilic crosslinker has the formula (II):

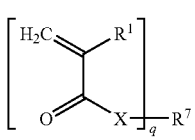

wherein $R^1$ is H or $CH_3$; $R^7$ is substituted or unsubstituted $C_1$-$C_{300}$ alkyl, aryl, alkaryl, arylalkyl or heteroaryl; X=O; and q=2, 3 or 4.

9. The method according to claim 8, wherein $R^1$ is $CH_3$.

10. The method according to claim 8, wherein $R^1$ is H.

11. The method according to claim 7, wherein the hydrophilic crosslinker has the formula (III):

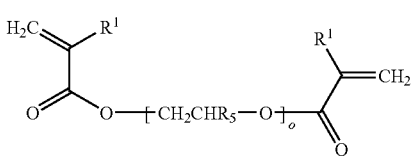

wherein $R^1$ and $R^5$ are independently H or $CH_3$; and
o is such that the number-average molecular weight is about 200 to about 2000.

12. The method according to claim 11, wherein o is 1-5.
13. The method according to claim 11, wherein $R^1$ is $CH_3$.
14. The method according to claim 11, wherein $R^5$ is H.

15. A flexible intraocular lens comprising a polymer obtained by polymerizing in a closed mould an acrylic monomer composition comprising a single high refractive index monomer according to formula (I):

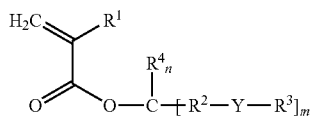

wherein $R^1$ is H or $CH_3$;
$R^2$ is a $C_1$-$C_3$ alkylene or —($C_1$-$C_3$ alkylene)-Y—($C_1$-$C_3$ alkylene)-;
Y is O or S;
$R^3$ is $C_6$-$C_{18}$ aryl or heteroaryl;
$R^4$ is H or linear or branched $C_1$-$C_6$ alkyl;
m+n=3;
n=0 or 1; and
m=2 or 3;
in the presence of an initiator that is activated by light having a wave length of 390 nm or more, wherein the intraocular lens is a flexible lens.

16. The flexible intraocular lens according to claim 15, wherein the intraocular lens has a glass transition temperature (Tg) of less than 25° C.

17. The flexible intraocular lens of claim 16 further having a refractive index of at least 1.50.

18. The flexible intraocular lens of claim 16 further having an elongation of at least 150%.

19. The flexible intraocular lens according to claim 15, wherein m=3 and n=0.

20. The flexible intraocular lens according to claim 15, wherein the acrylic monomer composition further comprises a hydrophilic crosslinker.

21. The flexible intraocular lens according to claim 20, wherein the hydrophilic crosslinker has the formula (II):

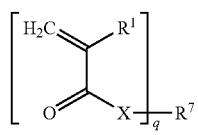

wherein $R^1$ is H or $CH_3$; $R^7$ is substituted or unsubstituted $C_1$-$C_{300}$ alkyl, aryl, alkaryl, arylalkyl or heteroaryl; X=O; and q=2, 3 or 4.

22. The flexible intraocular lens according to claim 20, wherein the hydrophilic crosslinker has the formula (III):

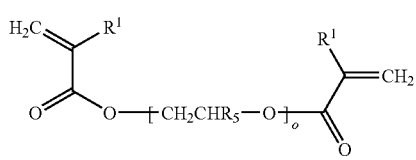

wherein $R^1$ and $R^5$ are independently H or $CH_3$; and
o is such that the number-average molecular weight is about 200 to about 2000.

23. A polymer obtained by polymerizing in a closed mould an acrylic monomer composition comprising a single high refractive index monomer according to formula (I):

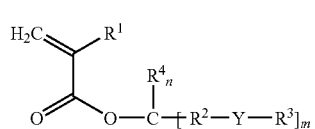
(I)
wherein $R^1$ is H or $CH_3$;
$R^2$ is a $C_1$-$C_3$ alkylene or —($C_1$-$C_3$ alkylene)-Y—($C_1$-$C_3$ alkylene)-;
Y is O or S;
$R^3$ is $C_6$-$C_{18}$ aryl or heteroaryl;
$R^4$ is H or linear or branched $C_1$-$C_6$ alkyl;
m+n=3;
n=0 or 1; and
m=2 or 3;
in the presence of an initiator that is activated by light having a wave length of 390 nm or more.
* * * * *